United States Patent [19]

Suzuki et al.

[11] 3,970,690
[45] July 20, 1976

[54] METHOD FOR PREPARING DISPERSING AGENT

[75] Inventors: Shigeyuki Suzuki, Sagamihara; Akira Yamauchi, Urawa; Shoji Kiyama, Tokyo; Kiyoshi Yamaki, Fuchu, all of Japan

[73] Assignee: Kureha Kagaku Kogyo Kabushiki Kaisha, Tokyo, Japan

[22] Filed: Feb. 27, 1974

[21] Appl. No.: 446,224

Related U.S. Application Data

[63] Continuation-in-part of Ser. No. 168,495, Aug. 2, 1971, abandoned.

[52] U.S. Cl. .............................. 260/505 C; 208/40; 106/96
[51] Int. Cl.² ........................................ C07C 143/24

[58] Field of Search ........ 208/40; 260/505 R, 505 C

[56] References Cited

UNITED STATES PATENTS

| | | | |
|---|---|---|---|
| 2,413,855 | 1/1947 | Berl et al. | 260/505 |
| 3,617,477 | 11/1971 | Gomi et al. | 208/40 |

*Primary Examiner*—James O. Thomas, Jr.
*Assistant Examiner*—A. Siegel
*Attorney, Agent, or Firm*—Wenderoth, Lind & Ponack

[57] ABSTRACT

An improved dispersing agent for cement having low foamability and high dispersibility is prepared by sulfonating high aromatic hydrocarbon compounds, and subsequently neutralizing the sulfonated compounds.

1 Claim, No Drawings

METHOD FOR PREPARING DISPERSING AGENT

CROSS REFERENCE TO RELATED APPLICATIONS

This is a continuation-in-part application of Ser. No. 168,495 filed on Aug. 2, 1971, now abandoned.

BACKGROUND OF THE INVENTION

This invention relates to a composition of a dispersing agent or dispersant for cement which is highly dispersible and low in foamablity, and a method for preparing the same. More particularly, it is concerned with an improved dispersant, in which a mixture of hydrocarbon compounds of high aromaticity obtained by heat-treating at a high temperature raw material hydrocarbon from petroleum or coal is subjected to sulfonation, and the sulfonated compound is then neutralized.

In general, a dispersing agent is effective in dispersing oil or fine particles of a solid substance into water. Most of the dispersing agents known heretofore, however, cause considerable foaming by agitation at the time of dispersion, or entrain air into the dispersion liquid to incorporate within the liquid numerous fine foams. While such foaming effect may, in some cases, be effectively utilized, it becomes very often a great problem. For example, a layer of foam on the surface of a liquid shields the liquid phase from the external atmosphere, which prevents the liquid from contacting the external atmosphere and makes it difficult to observe the condition of the liquid surface. This foaming phenomenon, therefore, constitutes a considerable obstacle in the practical aspect. Another disadvantage arising from such foaming is that, in the field of ceramics industry where slurry or paste prepared by dispersing powder particles of a solid material into water is used, the layer of foam created on the liquid surface impairs moldability of the slurry or pasty material, or the foams created by entrained air in the dispersion result in molded articles of high porosity, lowering the mechanical strength of the shaped products.

Under the circumstances, it has been the long-felt need that an improved dispersing agent which is causes less foaming and possesses excellent dispersibility be developed.

SUMMARY OF THE INVENTION

It is thus the object of the present invention to provide dispersant compositions for cement.

Another object is to provide dispersant compositions for cement which cause less foaming and are as readily dispersible.

Further object of the present invention is to provide a process for producing such dispersant compositions.

The dispersant composition for cement in accordance with the present invention comprises a water-soluble alkali sulfonate of a pitch which is an aromatic mixture comprising at least 80% thereof of a component predominantly having a fused-ring structure having at least three aromatic rings therein, with or without an alkyl side chain, and having an average molecular weight of from 500 to 2,000. The sulfonate is produced by a process which comprises the steps of:

1. sulfonating the pitch with a sulfonating agent such as chlorosulfonic acid, sulfuric anhydride, fuming sulfuric acid, or concentrated sulfuric acid,
2. neutralizing the pitch sulfonic acid with an alkali such as NaOH, $Na_2CO_3$, KOH, $K_2CO_3$, $Ca(OH)_2$, gaseous $NH_3$ or aqueous $NH_3$ to produce the sulfonate.

The starting pitch is obtained by thermal cracking of a hdyrocarbon oil originated from petroleum or coal at a high temperature of 700° to 2,000°C to obtain an oily product as well as a gaseous product such as acetylene, ethylene and the like, removing the gaseous product from the oily product and removing from the oily product a lower molecular weight material such as benzene or toluene by distillation or extraction thereby obtaining a tarry material as the pitch.

The thus formed pitch-sulfonate is added to cement in a quantity of 0.2 to several percent to provide excellent abiltiy as a dispersant for cement.

The nature and details of the present invention will become more apparent from the following detailed description of the invention, when read in connection with preferred examples thereof.

DETAILED DESCRIPTION OF THE INVENTION

Nature of a starting pitch used in the present invention is closely related to the cement dispersing ability of a pitch-sulfonate obtained by sulfonating the pitch, and particularly the average molecular weight, the distribution thereof and aromaticity of the pitch are important factors. While it has not yet been explained theoretically, many experiments lead to the conclusion that such a pitch should be used in accordance with the present invention which is a mixture of aromatic compounds comprising at least 80% of a component mainly having a fused-ring structure of at least three rings therein, with or without an alkyl side chain, and having an average molecular weight of 500 – 2,000, said pitch also having a carbon content of at least 90% by elemental analysis, a H/C - atomic ratio of 0.35 - 1.0 and a softening temperature of higher than or equal to 150°C. Such a pitch, usually, contains less than about 20% of a fraction insoluble in quinoline or nitrobenzene and less than several percent of a fraction insoluble in heptane.

When the average molecular weight is less than 500, the resulting sulfonated pitch has low dispersion effect for cement, or even if it has some dispersion effect, it also has much foaming effect; in any event the unique combination of ready dispersability and high foamability as a dispersant for cement according to the present invention is not realized. When the average molecular weight is over 2,000, on the other hand, a part of the resultant sulfonate of the pitch is insoluble in water; or even if it is soluble in water, the viscosity of the aqueous solution thereof is high and such a pitch-sulfonate is not appropriate in use or in processing. Further, in this case of high molecular weight, formation of by-products is accelerated in a sulfonation step, thereby reducing a yield of the desired pitch sulfonate. Accordingly, an average molecular weight of a pitch is optimum in a range 500 – 2,000.

However, it is difficult and unnecessary to demonstrate that all the components of the pitch have a molecular weight in the range of 500 – 2,000. This is because molecular weight measurement can be done as to a soluble part in an organic solvent and a usual pitch contains some fractions insoluble in an organic solvent.

The method of molecular weight measurement used in the present invention is one in which a molecular weight is measured based on the relationship between a vapor pressure increment of a solvent and a concentration of a solute, which method is resorted to for ordinary high polymer compounds. Nitrobenzene is used. Therefore, a value of the average molecular weight of a pitch given hereinafter is measured for the fraction soluble in nitrobenzene. When the nitrobenzene insoluble fraction content is beyond 20% of a pitch, even if the measured-value of the molecular weight is not beyond 2,000, a content of the water-insoluble fraction in the resulting sulfonated pitch is increased unreasonably. Consequently, it can be considered that the pitch containing more than or equal to 80% thereof of components having an average molecular weight of 500 – 2,000, when measured by the method described above, is an optimum starting pitch in the present invention. Limitations of carbon content and H/C atomic ratio, both of which are derived from an elemental analysis of a pitch, and a limitation of a softening point are defined experimentally as indications of aromaticity of a pitch.

The pitch is produced by heat treatment of a hydrocarbon oil at a temperature of 700° to 2,000°C whereby the oil is thermally cracked into a gaseous product and an oily or tarry product from which the pitch is obtained. The hydrocarbon oil undergoes remarkable chemical change, when subjected to a high temperature heat treatment. While the mechanism of the chemical change has yet to be fully clarified, the principal reactions are pyrolysis of the hydrocarbons under a high temperature, and polycondensation of the pyrolytic products. The resultant liquid tarry product or solid pitchy product is extremely abundant in aromaticity, and does not contain aliphatic hydrocarbons.

More surprisingly, by proper selection of the heat-treating conditions, it is always possible to obtain a high aromatic product or extremely similar properties in spite of using various hydrocarbon oils.

The heat-treatment condition above referred to, permitting slight differences depending on types of the hydrocarbon oil to be used, is to heat the material such as, for example, petroleum hydrocarbons including crude oil, naphtha, kerosene, heavy oil etc. at a temperature of from 700°C to 2,000°C, for a reaction time of from 0.005 second to 1.0 second and then cool the heated material by an arbitrary method. In the case of coal hydrocarbons, the heat-treatment may sometimes be carried out at the same temperature level as that for the petroleum hydrocarbons with a longer reaction time than that of the former.

The resultant product from the heat-treatment is divided into two major classes of gaseous product including hydrogen, acetylene, olefins, etc., and oily product. The oily product is further separated into a light fraction such as benzene, toluene, etc. and a heavy fraction such as a tar which can be used as the pitch in accordance with the present invention if it has characteristics called for by the present invention.

The tarry product thus obtained has been found, through chromatography, nuclear magnetic resonance spectrum, infrared absorption spectrum, and other instrumental analyses, to be a mixture of various materials, i.e., a mixture of various fused polycyclic aromatic compounds having different molecular weight, in which not only are aliphatic hydrocarbon molecules absent, but also aliphatic side chains are only slightly present.

For the purpose of removing light components from the oily fraction or the tarry product to obtain such a pitch as is a mixture of fused polycyclic compounds in accordance with the present invention, distillation such as for example vacuum distillation, or steam distillation etc., or extraction is adoptable. Further, it is also preferable, for the purpose of increasing molecular weight of the pitch, that the oily product is treated thermally at a temperature of from 350° to 600° C for a period of from 1 minute to 300 minutes prior to the above-described operation.

The oily product separated from the gaseous product can be subjected to a single fractionation step to remove therefrom a lighter fraction or lower molecular fractions thereby to produce the pitch to be used in the present invention. However, it is preferable to subject the oily product to the first fractionation to remove a light fraction such as benzene or toluene and then to the second fractionation to further remove a light fraction thereby to obtain the pitch.

The pitch thus produced is then subjected to sulfonation. The sulfonation reaction may be of any kind which has so far been known generally. For example, the sulfonation by concentrated sulfuric acid, fuming sulfuric acid, chlorosulfonic acid, sulfuric anhydride, etc. well meets the present purpose. The degree of sulfonation can be appropriately adjusted in accordance with the conditions for sulfonation.

The product from the sulfonation reaction is then neutralized with an inorganic base such as gaseous or aqueous ammonia, caustic soda, caustic potash, calcium hydroxide, sodium carbonate, potassium carbonate, sodium phosphate, and so forth. The sulfonate salt of the fused-ring aromatic hydrocarbons produced by the neutralization may be used in the state of a mixture with other salts produced as byproducts during the neutralization reaction, although it is of course possible to use it after separating these by-product salts therefrom depending on necessity. It is possible to use the sulfonate of the fused-ring aromatic hydrocarbon compound with addition of adjuvants such as other salts and a surfactant.

The sulfonate salt of the fused-ring aromatic hydrocarbon thus obtained possesses the above mentioned particular chemical structure, and is useful as a dispersing agent in a variety of fields. For example, in the field of refractory manufacturing where clay paste, clay slurry, castables, etc. are prepared, if the dispersant according to the present invention is added to the clay mixture, not only its handling becomes facilitated due to no foaming effect, but also a compact shaped body of increased mechanical strength can be obtained. Same result is also obtainable in the case of molding carbon articles with clay as the binder. This dispersant also finds use in suctioning sludge at the time of underground boring for petroleum mining, or in preparing a slurry for mud circulation in civil engineering works. In case it is used as the dispersant for preparing cement mixture, no air is entrained in flesh concrete, so that the resulting cured concrete maintains its required mechanical strength. Hence, the dispersing agent according to the present invention is particularly advantageous in obtaining cured concrete of high mechanical strength.

While the dispersing agent according to the invention is less foamy, it is sometimes required, in the case of flesh concrete, for example, to introduce air into the cement mixture to increase workability of the cured concrete as well as its durability against freezing and melting, for the purpose of which an air-entraining agent is added from time to time.

In such a case as above, a pitch sulfonate in an amount of from 0.2 to 1.0 wt% of cement is sufficiently effective, but, several percent of pitch sulfonate added to cement does not hinder at all the hardening of the modified cement.

When the dispersing agent according to the present invention is used together with such air-entraining agent, the effects of both additives act on the mixture material, hence the dispersant becomes useful as one having air-entraining effect.

PREFERRED EMBODIMENT

In order to enable persons skilled in this field of art to readily practice the present invention, the following examples are presented. It should, however, be noted that these examples are merely illustrative, and that any change and modification therein may be permitted within the spirit and scope of the present invention as set forth in the appended claims.

Table 1

| (Recipe of Cement Mixture) | | |
|---|---|---|
| Ingredient | | Quantity (kg.) |
| Cement | ("Asano" brand, product of Nippon Cement Co., Ltd.) | 15.0 |
| Gravel | (10 mm sieve and above) | 41.2 |
| Gravel | (10 mm sieve and below) | 13.8 |
| Sand | (0.6 mm sieve and above) | 23.3 |
| Sand | (0.6 mm sieve and below) | 15.7 |
| Water | | 9.2 |

The test results on the cement mixtures containing varying quantities of the dispersant according to the present invention are as shown in the 2, Table 2, from which it will be recognized that, with increase in the amount of dispersing agent, a remarkable water reducibility can be attained, which contributes to increase in the mechanical strength of cured cement.

Table 2

(Test Results on Cement Mixtures with Varying Quantities of the Dispersing Agent According to the Present Invention)

| Run No. | Quantity(*) of Dispersant Added (%) | Rate of() Reduction in Quantity of Water Added (%) | Quantity(*) of Air Entrained (%) | (*) Slump (cm) | Compression(*) Strength (kg/cm²) | |
|---|---|---|---|---|---|---|
| | | | | | 7th day | 28th day |
| 1 | — | — | 2.1 | 18.1 | 127 | 247 |
| 2 | 0.1 | 3.8 | 2.0 | 17.7 | 133 | 258 |
| 3 | 0.3 | 7.2 | 2.0 | 18.1 | 139 | 276 |
| 4 | 0.5 | 10.9 | 1.9 | 17.9 | 145 | 284 |

(NOTE)
*Percentum by weight with respect to cement.
**The rate is with respect to the water content in the cement mixture without addition of the dispersing agent according to the present invention by taking the water content as 100.
***Quantity of air entraining, slump, and compression strength are measured on the basis of Japanese Industrial Standards, i.c., JIS A-1128-1960, and JIS A-1108-1963.

EXAMPLE 1

Heavy naptha was subjected to heat-treatment at 1,100°C for 0.04 second in an internal heating type reactor to obtain gaseous substance containing acetylene and ethylene together with oily or tarry product.

This tarry product was distilled at a temperature up to 250°C level under a reduced pressure of 5 mm Hg to obtain pitch residue. As the result of various instrumental analyses, it was found that the substance was a mixture of hydrocarbon compounds having various fused-ring aromatic structures. The average molecular weight of the pitch was 1100. The elemental analysis showed that the carbon content was 95 wt % and the H/C atomic ratio was 0.53, and further the softening point was 200°C, and nitrobenzene-insoluble fraction was 10% by weight thereof.

30 g. of this pitch was treated with 40 g. of sulfuric anhydride at a temperature of 80°C for 3 hours, after which it was neutralized by adding thereto calcium hydroxide, $Ca(OH)_2$, precipitated and filtered. The filtered product was concentrated and dried to obtain 80 g. of dark brown powder.

The thus obtained powdery material was added in various quantities into a cement mixture of the recipe as shown in Table 1 below.

EXAMPLE 2

30 g. of sulfonated pitch of the same quality as obtained in Example 1 was neutralized by sodium hydroxide to obtain 76 g. of dark brown powder of the sulfonate.

The thus obtained dispersant was added in various quantities into a cement mixture for air-entrained concrete of the recipe as shown in Table 3 below.

Table 3

| (Recipe of Cement Mixture) | | |
|---|---|---|
| Ingredient | | Quantity (kg) |
| Cement | ("Portland" cement, product of Onoda Cement Co.) | 15.0 |
| Gravel | (10 mm sieve and above) | 44.1 |
| Gravel | (10 mm sieve and below) | 14.7 |
| Sand | (0.6mm sieve and above) | 22.3 |
| Sand | (0.6mm sieve and below) | 15.0 |
| Water | | 8.3 |

The test results on the cement mixtures containing varying quantities of the dispersant according to the present invention are as shown in the following Table 4, from which it will be recognized that excellent air-entraining effect and water reducing effect could be attained.

Table 4

(Test Results on Cement Mixtures with Varying Quantities of the Dispersing Agent According to the Present Invention)

| Run No. | Quantity of Dispersant Added (%) | **** Quantity of Air-Entraining Agent Added (%) | Rate of Reduction in Quantity of Water Added (%) | Quantity of Air Entrained (%) | Slump (%) | Compression Strength (kg/cm²) | |
|---|---|---|---|---|---|---|---|
| | | | | | | 7th day | 28th day |
| 1 | — | — | — | 1.5 | 7.2 | 179 | 335 |
| 2 | 0.25 | — | 4.2 | 1.2 | 7.3 | 221 | 368 |
| 3 | 0.35 | 0.006 | 15.7 | 5.3 | 7.5 | 246 | 394 |
| 4 | 0.25 | 0.005 | 13.3 | 5.2 | 8.3 | 231 | 381 |
| 5 | 0.15 | 0.004 | 10.8 | 4.2 | 8.3 | 233 | 397 |

(NOTE)
****A nonionic surfactant manufactured and sold by Onoda Unilon Co., Japan, under a trademark "Hi-Foam". Quantities of the dispersant and air-entraining agent added are based on percentum by weight with respect to total cement.

EXAMPLE 3

Crude petroleum of Kuwait origin preheated to 300°C was atomized at a rate of 1 kg/hr. into steam which has been super-heated to approximately 2,000°C by a regenerative furnace using zirconia pebbles as a heat-storing medium and fed at a rate of 5 kg/hr.

The crude pertroleum oil was caused to contact the high temperature steam at a temperature range of from 1,100°C to 1,200°C for 0.06 second, and subsequently cooled, whereby 700 l/hr. of a gaseous product and 450 g/hr. of a tarry product were obtained.

This tarry product was distilled under a reduced pressure of 5 mm Hg and up to a temperature level of 200°C to quinoline-insoluble pitch residue of 230 g/hr. The same analyses as those conducted in Example 1 above were conducted. The pitch residue was recognized to be a mixture of hydrocarbon compounds having various kinds of fused-ring aromatic structures. Then, the average molecular weight of the pitch was recognized to be 850, the result of the elemental analysis of the pitch showed a carbon content of 93 wt. % and a H/C atomic ratio of 0.70, and the softening point was 180°C, and both the nitrobenzene-insoluble content and the quinolineinsoluble content were less than 1 wt. %.

The pitch was sulfonated in the same manner as in Example 1 and then neutralized with sodium hydroxide. The thus obtained sodium salt of sulfonated pitch was applied to an alumina-castable to obtain the result as shown in Table 5 below. From the results shown, it will be understood that the dispersant according to the present invention helps reduce the quantity of water required to adjust the castable paste as well as reduce porosity of the cast product and increase mechanical strength thereof.

Table 5

| | No Addition | Sulfonated Pitch Added (0.2 wt.%) |
|---|---|---|
| Water (%) | 16.5 | 13.0 |
| Porosity (%) | 32.4 | 29.3 |
| Compression Strength (kg/cm²) | | |
| after curing | 170 | 300 |
| after drying | 160 | 180 |
| after firing | 240 | 310 |

(NOTE)
1) Ingredients:

Table 5-continued

| | No Addition | Sulfonated Pitch Added (0.2 wt.%) |
|---|---|---|
| Alumina cement | | 10% by weight with respect to aggregate |
| Aggregate | | Schamotte sand |

2) Curing:
   at room temperature for 24 hrs.
3) Drying:
   at 105°C for 10 hrs.
4) Firing:
   at 1,400°C

EXAMPLE 4

The same sodium salt of sulfonated pitch as obtained in Example 3 above was used in manufacturing clay-bonded graphite brick.

It was found that, when the dispersant according to the present invention was added, the quantity of water to be added in preparing paste could be reduced, while still maintaining sufficient plasticity and workability of the paste, and the final, fired product possessed excellent mechanical strength as shown in Table 6 below.

Table 6

| | No Addition | Sulfonated Pitch Added (0.2 wt.%) |
|---|---|---|
| Water (%) | 17.1 | 16.6 |
| Porosity (%) | 25 | 23.7 |
| Shrinkage during drying (%) | 3.82 | 3.75 |
| Compression Strength (kg/cm²) | | |
| after drying | 295 | 354 |

What we claim is:

1. A dispersant composition which comprises a water-soluble alkali sulfonate of a pitch, said pitch
   1. being an aromatic mixture containing at least 80% thereof of a component predominantly having a fused-ring molecular structure of at least three rings and having an average molecular weight of from 500 to 2,000,
   2. having a carbon content of at least 90% based on elemental analysis, a hydrogen to carbon atomic ratio of 0.35 to 1.0 and a softening temperature of at least 150°C, and
   3. containing less than about 20% of a fraction insoluble in nitrobenzene, said alkali being selected from the group consisting of sodium, potassium, calcium and ammonium.